United States Patent
Ostler et al.

(10) Patent No.: US 8,944,820 B2
(45) Date of Patent: Feb. 3, 2015

(54) DENTAL RESTORATIVE COMPOSITE WITH LUMINESCENT CRYSTALS

(71) Applicant: DENTSPLY International Inc., York, PA (US)

(72) Inventors: Calvin Ostler, Riverton, UT (US); Hui Lu, Magnolia, DE (US)

(*) Notice: Subject to any disclaimer, the term of this patent is extended or adjusted under 35 U.S.C. 154(b) by 13 days.

(21) Appl. No.: 13/909,549

(22) Filed: Jun. 4, 2013

(65) Prior Publication Data

US 2013/0323685 A1 Dec. 5, 2013

Related U.S. Application Data

(60) Provisional application No. 61/654,986, filed on Jun. 4, 2012.

(51) Int. Cl.
| | | |
|---|---|---|
| *A61C 5/00* | (2006.01) | |
| *A61K 6/083* | (2006.01) | |
| *A61C 13/15* | (2006.01) | |
| *A61K 6/00* | (2006.01) | |

(52) U.S. Cl.
CPC .............. *A61K 6/083* (2013.01); *A61C 19/003* (2013.01); *A61K 6/0097* (2013.01)
USPC .......................... 433/215; 433/228.1; 106/35

(58) Field of Classification Search
USPC .................. 433/215, 228.1; 106/35
See application file for complete search history.

(56) References Cited

U.S. PATENT DOCUMENTS

| | | | |
|---|---|---|---|
| 6,008,264 A | 12/1999 | Ostler et al. | |
| 6,730,715 B2 * | 5/2004 | Jia | 523/115 |
| 6,783,810 B2 | 8/2004 | Jin et al. | |
| 7,314,610 B2 * | 1/2008 | Loveridge | 424/9.7 |
| 2004/0196538 A1 * | 10/2004 | Burgener et al. | 359/341.5 |
| 2006/0194172 A1 * | 8/2006 | Loveridge | 433/215 |
| 2006/0194895 A1 * | 8/2006 | Loveridge et al. | 523/115 |
| 2008/0057000 A1 * | 3/2008 | Loveridge | 424/9.7 |
| 2011/0200971 A1 | 8/2011 | Kalgutkar et al. | |

FOREIGN PATENT DOCUMENTS

WO 97/33922 A1 9/1997

OTHER PUBLICATIONS

Q. Huang, et al., "Synthesis and Characterization of Highly Efficient Near-Infrared Upconversion Sc3+/Er3+/Yb3+ Tridoped NaYF4", J. Phys. Chem. C 2010, 114, pp. 4719-4724.
M. Uo, E, Kudo et al., "Preparation and Properties of Dental Composite Resin Cured Under Near Infrared Irradiation", Journal of Photopolymer Science and Technology, vol. 5, No. 5 (2009), pp. 551-554.

(Continued)

*Primary Examiner* — Ralph Lewis
(74) *Attorney, Agent, or Firm* — McNees Wallace & Nurick LLC

(57) ABSTRACT

A dental restorative composite and a method of curing the composite are disclosed in which the composite includes a polymerizable organic resin, a radiation activated initiator having an activation wavelength, an inert filler; and luminescent crystals, wherein the luminescent crystals emit radiation at a predetermined wavelength matching the initiator activation wavelength when the luminescent crystals are irradiated with radiation having a wavelength longer than the activation wavelength, the luminescent crystals being up-converting particles that result in those particles emitting radiation at a wavelength that initiates curing.

22 Claims, 2 Drawing Sheets

(56) References Cited

OTHER PUBLICATIONS

Alexander Stepuk, Dirk Mohn, Robert N. Grass, Matthias Zehnder, Karl W. Kramer, Fabienne Pelle, Alban Ferrier and Wendelin J. Stark, "Use of NIR light and upconversion phosphors in light-curable polymers," SciVerse ScienceDirect (www.sciencedirect.com), p. 304-3011, Nov. 22, 2011.

Li Li, Cao Xue-Qin, Zhang You and Guo Chang-Xin, "Synthesis and upconversion luminescence of Lu2O3:Yb3 +, Tm3+ nanocrystals," Science Direct (www.sciencedirect.com), p. 373-379, Sep. 22, 2011.

Chunxia Li, Zewei Quan, Piaoping Yang, Jun Yang, Hongzhou Lian and Jun Lin, "Shape controllable synthesis and upconversion properties of NaYbF4/NaYbF4:Er3+ and YbF3/YbF3:Er3+ microstructures," Journal of Materials Chemistry (www.rsc.org/materials), p. 1353-1361, Jan. 9, 2008.

Elixir William Barrera, Maria Cinta Pujol, Francesc Diaz, Soo Bong Choi, Fabian Rotermund, Kyung Ho Park, Mun Seok Jeong and Concepcion Cascales, "Emission properties of hydrothermal Yb3+, Er3+ and Yb3+, Tm3+—codoped Lu2O3 nanorods: upconversion, cathodoluminescence and assessment of waveguide behavior," Nanotechnology 22 (2011) 075205, p. 1-15, Jan. 14, 2011.

\* cited by examiner

DENTAL RESTORATIVE COMPOSITE WITH LUMINESCENT CRYSTALS

CROSS-REFERENCE TO RELATED APPLICATIONS

This application claims the benefit of and priority to U.S. Provisional Application No. 61/654,986 filed Jun. 4, 2012, which is hereby incorporated by reference in its entirety.

FIELD

The present invention relates to curable dental restorative composites and more particularly to curable dental composites containing luminescent crystals.

BACKGROUND

Curable dental composites are widely used in dentistry to fill cavities. Dental composites with excellent tooth-like appearance can be formed on command with the advance of photopolymerization technology. The composites may contain a variety of materials and include monomers and a photoinitiator that generates initiating species (most commonly initiating radicals for majority of commercial dental composites) when exposed to a particular wavelength, thereby initiating polymerization of the monomers to cure the composite. Based on the mechanism by which initiating radicals are generated, photoinitiators for free radical polymerization are generally divided into two groups: 1) Norrish Type I photoinitiators, which undergo a unimolecular bond cleavage/dissociation upon irradiation to generate free radicals and 2) Norrish Type II photoinitiators, which undergo a bimolecular reaction where the excited state of the photoinitiator interacts with a co-initiator, forming excited state complex and to yield free radicals. There are many Norrish Type I and Type II photoinitiators for UV-curing applications, whereas relatively limited photoinitiators (mostly Type II) for visible light irradiation source.

However, visible blue light can also be scattered and absorbed by enamel and dentin, and certain down-conversion into longer wavelengths by way of fluorescence (such as 520 nm fluorescence emission by 410 nm excitation). As a dentist attempts to cure a dental composite by illuminating the tooth and composite from the top of the restoration and/or by directing the light from the side through dentin and enamel, much of the trans-tissue blue light is taken by way of attenuation (primarily light scattering, with certain absorption and fluorescence). As a result, this requires relatively high intensity (Irradiance) of visible blue light to penetrate through natural tooth structure.

Furthermore, clinical procedures using conventional composites have traditionally required building up the composite layer by layer. The incremental or layering placement is necessary due to polymerization shrinkage stress and depth of cure limitations. Restricted polymerization shrinkage, as one of the major drawbacks of dental composites, results in disrupting shrinkage stress at the interface between the composites and tooth, and can be transferred to the tooth structure.

Near infrared energy from about 800 nm to about 1200 nm ("Near-IR Therapeutic Window") passes through natural dentition with little absorption and scattering, thus achieving significantly deeper penetration as compared to blue light (peak emission~470 nm) radiation and was used in luminescent up-conversion of certain dental materials in Stepuk, A., et. al., "Use of NIR light and up conversion phosphors in light-curable polymers", Dental Materials 28, (2012) 304-311. In this reference, the sodium salt of a yttrium fluoride host was co-doped with 25% ytterbium and 0.3% thulium ($\beta$-NaYF$_4$:25%Yb$^{3+}$, 0.3%Tm$^{3+}$). The preparation was a solid salt that was then balled milled to particle diameters in the 2-3 micrometer range and incorporated into a dental adhesive (Heliobond).

Despite the use of a dental adhesive, the teachings of Stepuk are not transferable to the dental arts and there remain numerous voids not met by Stepuk. Among other unsatisfactory results, closer inspection of this reference reflects that upwards of 90 watts of 980 nm energy was applied to obtain 1 milliwatt of usable 490 nm radiation, which corresponds to an efficiency of approximately 0.001%. Accordingly, the teachings of Stepuk are not directly extendible to actual dental applications because the power required to achieve a useful result would cause an unacceptable temperature rise in the tooth pulp or other surrounding tissue. Stepuk also fails to teach any particle loading of greater than 20%, which would not even be sufficient to render it a dental composite and does not account for other constituents that might be included in the composite that further impact the effectiveness of the up-conversion.

SUMMARY

Exemplary embodiments are directed to dental composites and methods of curing the dental composites that overcome these and other drawbacks by providing curable dental composites containing luminescent fillers that employ host materials and concentrations of dopants that are more efficient, require less power to energize, and pose less risk to surrounding dental tissue, while accounting for inert fillers and other ingredients that may be included in dental composites.

According to an exemplary embodiment, a dental composite comprises a polymerizable monomer; a radiation activated initiator having an activation wavelength; an inert filler; and luminescent crystals. The luminescent crystals emit radiation at a predetermined wavelength matching the initiator activation wavelength when the luminescent crystals are irradiated with radiation that has a wavelength that is longer than the initiator activation wavelength, typically wavelengths in excess of 780 nm and more typically, near-infrared radiation (also referred to as NIR) in the range from about 780 nm to about 1064 nm.

In certain embodiments the crystals employ a lanthanide fluoride, salt, or oxide host doped with one or more lanthanide ions.

According to another exemplary embodiment, a method of curing a dental composite includes providing a dental composite as described herein, filling a cavity formed in a tooth with the provided dental composite and irradiating the composite with radiation from a curing light having a laser source that emits radiation at a pre-determined fixed wavelength in the near-infrared range of the spectrum. The emitted radiation at the pre-determined fixed wavelength causes the luminescent crystals to emit radiation at the activation wavelength of the initiator.

DETAILED DESCRIPTION OF EXEMPLARY EMBODIMENTS

Figure 1:
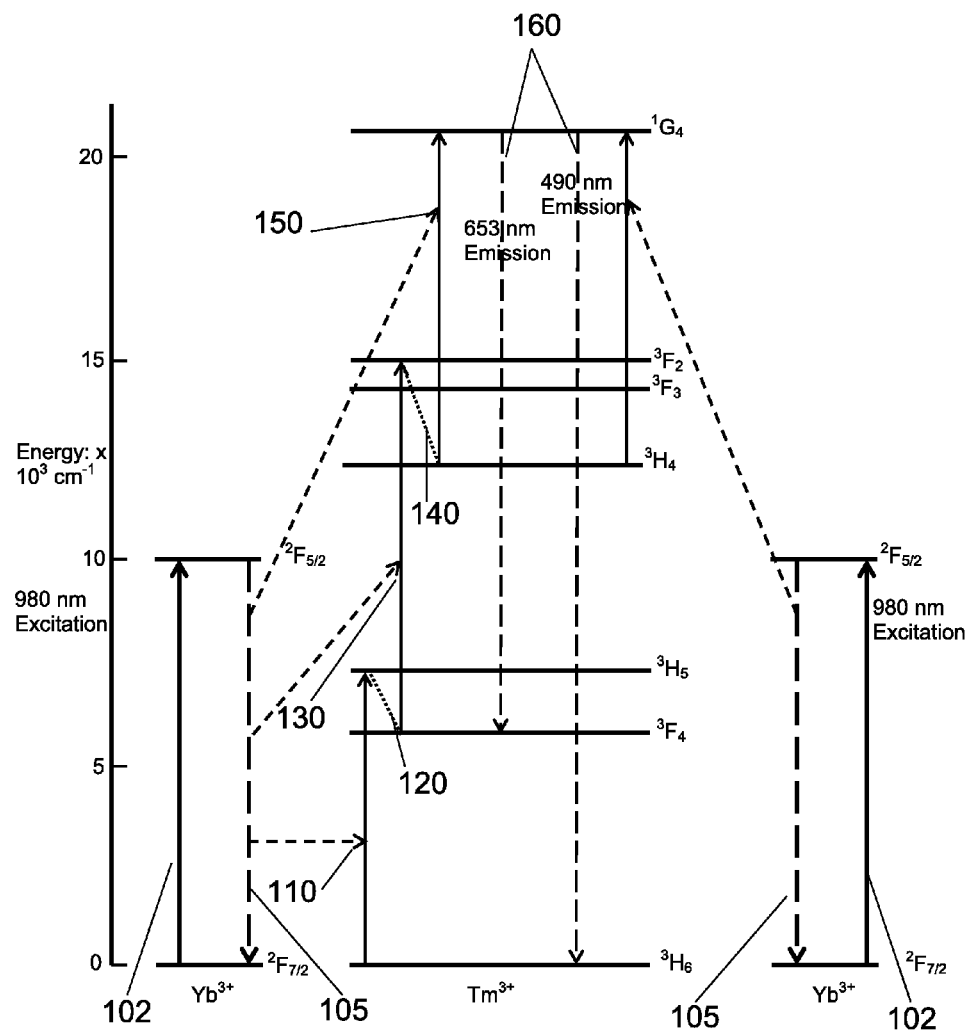
FIG. 1 is an electron diagram that schematically illustrates the radiation emission of luminescent crystals in accordance with one exemplary embodiment.

Exemplary embodiments are directed to dental composite formulations containing up-converting luminescent crystals that emit radiation at a wavelength corresponding to the photoinitiator activation. As a result of the luminescent crystals and photoinitiator being dispersed in the composite (and thus in the cavity when used as a filling), restoration with more uniform material property and shrinkage stress distribution can be achieved. Furthermore, a more uniform stress distribution can lead to less shrinkage stress concentration on the cavity floor and lessen damage to tooth-composite bonding, as numerous studies have shown that conventional composites tend to pull away from the cavity floor due to the polymerization shrinkage stress when light cured from the occlusal surface in the ordinary manner.

In luminescent materials, a host allows many joules of energy to enter the host's matrix and allow absorption and emission centers that are scattered throughout the host by doping to absorb energy until a population inversion of electrons at a given level is obtained. At that time there is a cascade of this inversion that produces a pulse of photons of a particular wavelength that are the precursor to the radiation emitted from the overall system.

In such systems the host material may have little influence on the phonon energy as the input energy is either overwhelming, or of a specific non-interfering wavelength, or both. Further, in these crystal laser systems, higher energy wavelengths are used as the pumping source to produce lower energy wavelengths. For instance in a erbium-doped yttrium-aluminum-granite host laser (Er:YAG laser), the pump wavelength is 885 and/or 1532 nanometers (nm) the emitted wavelength is the much lower in energy and longer wavelength 2940 nm. Equally illustrative of the point is neodymium absorption and emission center hosted by the same materials absorb energy at 808 nm and emit energy at 1264 nm, again a longer, lower energy wavelength. These lasers are relatively efficient, in the range of 33% and up. In such cases the effect exerted on the phonon energy of the system is negligible. However, during phosphor up-converting one is going from a lower energy level, longer wavelength of absorption energy, such as 980 nm and obtaining an emission of a much higher energy and shorter wavelength of, for example, 490 nm.

Dental composites in accordance with exemplary embodiments include a polymerizable organic resin, a radiation activated initiator, an inert filler, and luminescent crystals, and may further include one or more other constituents.

The polymerizable organic resin may be any polymerizable monomer and/or oligomer, but is typically one or more (meth)acrylates or other free radically polymerizable compounds. Exemplary polymerizable monomers include mono-, di- or multi-methacrylates and acrylates such as 2,2-bis[4-(2-hydroxy-3-methacryloyloxypropoxy)phenyl] propane (Bis-GMA), 1,6-bis(2-methacryloxyethoxycarbonylamino)-2,4,4-trimethylhexane (UDMA), 2,2-bis[4-(methacryloyloxy-ethoxy)phenyl] propane (or ethoxylated bisphenol A-dimethacrylate) (EBPADMA), isopropyl methacrylate, triethyleneglycol dimethacrylate (TEGDMA), diethyleneglycol dimethacrylate, tetraethyleneglycol dimethacrylate, 3-(acryloyloxy)-2-hydroxypropyl methacrylate, 1,3-propanediol dimethacrylate, 1,6-hexanediol dimethacrylate (HDDMA), pentaerythritol triacrylate, pentaerythritol tetraacrylate, pentaerythritol tetramethacrylate, and combinations thereof, all by way of example.

The polymerizable monomer is present as about 15 to 25 percent by weight of the composite, typically about 17 to about 23% by weight. In certain embodiments, the polymerizable monomer is a combination of a high molecular weight component (such as Bis-GMA 513 g/mol and/or UDMA 471 g/mol, for example) and a low molecular weight component (such as TEGDMA 286 g/mol and/or HDDMA 254 g/mol, for example). In one embodiment, the polymerizable monomer is present at about 14 to about 18% by weight of the high molecular weight component and about 3 to about 5% by weight of the low molecular weight component in overall composite formulation.

Dental composites in accordance with exemplary embodiments also include inert filler particles and any inert filler particles that are suitable for use in dental compositions may be employed. The inert fillers provide the composite with desired physical properties such as increased mechanical strength, modulus, hardness, wear resistance, reduced thermal expansion, and polymerization volumetric shrinkage. Exemplary inert filler particles include, but are not limited to, strontium borosilicate, strontium fluoroalumino borosilicate glass, strontium alumino sodium fluoro phosphor-silicate glass, barium borosilicate, barium fluoroalumino borosilicate glass, barium aluminum-borosilicate glass, barium alumino borosilicate, calcium alumino sodium fluoro silicate, lanthanum silicate, lanthanum aluminosilicate, calcium alumino sodium fluoro phosphor silicate, and combinations thereof. Other filler particles include silicon nitrides, titanium dioxide, fumed silica, colloidal silica, quartz, kaolin ceramics, calcium hydroxy apatite, zirconia, and mixtures thereof.

Examples of fumed silica include OX-50 from DeGussa AG (having an average particle size of 40 nm), Aerosil R-972 from DeGussa AG (having an average particle size of 16 nm), Aerosil 9200 from DeGussa AG (having an average particle size of 20 nm), other Aerosil fumed silica might include Aerosil 90, Aerosil 150, Aerosil 200, Aerosil 300, Aerosil 380, Aerosil R711, Aerosil R7200, and Aerosil R8200, and Cab-O-Sil M5, Cab-O-Sil TS-720, Cab-O-Sil TS-610 from Cabot Corp.

The inert filler has a particle size in the range about 0.001 microns to about 50 microns.

Some or all of the inert filler particles can optionally be surface treated prior to incorporation into the composite composition. Surface treatments, particularly those using silane coupling agents or other compounds may be desirable for the inert filler particles to be more uniformly dispersed in the organic resin matrix, and also improve physical and mechanical properties. Suitable silane coupling agents include 3-methacryloxypropyltrimethoxysilane, 3-acryloxypropyltrimethoxysilane, 3-glycidoxypropyltrimethoxysilane, 3-mercaptopropyltrimethoxysilane, and mixtures thereof.

The inert filler particles form the bulk of the dental restorative composition and may be present in the dental composite in amounts of from about 56% to about 85% by weight of the dental restorative composite, such as from about 60% by weight to about 80% by weight percent, or from about 70% to about 75% by weight. In one embodiment, the inert filler particles are present at about 56% by weight, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, or about 85% by weight, or any range there between. It will further be appreciated, that in some embodiments, the luminescent crystal could completely replace the inert filler particles.

In one embodiment, the filler can comprise a mixture of a micron-sized radiopaque filler such as barium alumino fluoro borosilicate glass (BAFG, having an average particle size of about 1 micron) with nanofiller particles, such as fumed silica such as OX-50 from Degussa AG (having an average particle size of about 40 nm). In one embodiment, the concentration of micron-size glass particles ranges from about 70 weight percent to about 80 weight percent of the dental restorative composite, and the nanofiller sized inert filler particles can range from about 1 weight percent to about 10 weight percent of the composite.

The dental restorative composition also includes a photoinitiator. Any suitable photoinitiator that dissociates to form an initiating species may be employed, although the photoinitiator is preferably effective in the visible light spectrum range, such as those currently employed in other dental restorative applications. The activation wavelength of the photoinitiators may range from about 360 nm to about 520 nm, particularly from about 400 nm to 500 nm, although it will be appreciated that the specific range and peak activation (i.e. absorption) wavelength will depend upon the particular photoinitiator selected. For example, camphorquinone (CQ) absorbs energy preferentially in the visible blue spectrum (in the range of about 420 nm to 500 nm), having a peak absorption at 468 nm.

Exemplary suitable photoinitiators include diketone type initiators such as CQ, derivatives of diketone initiator, and acylphosphine oxide type photoinitiator such as diphenyl (2, 4, 6-trimethylbenzoyl) phosphine oxide (L-TPO), and combinations thereof. Other diketone type photoinitiator such as 1-phenyl-1,2 propanedione (PPD), and acylphosphine oxide type photoinitiator such as bis(2,4,6-trimethylbenzoyl)-phenylphosphine oxide (Irgacure 819), ethyl 2,4,6-trimethylbenzylphenyl phosphinate (Lucirin LR8893X), may also be used. Any of the foregoing may be used individually or in combination with one another.

The photoinitiator is present in an amount from about 0.05% to about 1.0% by weight, such as from about 0.08% to about 0.5% by weight or from about 0.1% to about 0.25% by weight of the dental restorative composition. Despite the relatively small amount of photoinitiator (which decreases the potential discoloration of the composition), the photoinitiator is still present in a sufficient amount to rapidly form a cured matrix throughout the entire cavity when the composition is exposed to radiation emitted by the luminescent crystals when those crystals are themselves irradiated with near-infrared radiation as subsequently discussed in more detail.

The polymerization initiator system of the composite may further include a polymerization accelerator, which may be a tertiary amine. One example of a suitable tertiary amine is ethyl 4-(dimethylamino)benzoate (EDAB). Other tertiary amines that may be used include 2-(ethylhexyl)-4-(N,N-dimethylamino)benzoate, 4-(dimethylamino) benzonitrile, and the like. The polymerization accelerator may be present in an amount of from about 0.03% to about 0.18% by weight of the dental restorative composition, such as from about 0.04% to about 0.15% by weight percent or from about 0.05% to about 0.12% by weight of the dental restorative composition.

Exemplary embodiments further incorporate luminescent crystals distributed throughout the dental restorative composition in an amount of about 0.1% to about 80% by weight of the dental restorative composite, typically about 0.1% to about 20% in embodiments employing both luminescent crystals and an inert filler. In some embodiments, the luminescent crystals are present at about 1% to about 20%, or from about 1% to about 10% by weight. In one embodiment, the luminescent crystals are present at about 1% by weight, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, or any range there between.

The distribution of the luminescent crystals in the restorative composition is preferably heterogeneous, which may be accomplished, for example, by incomplete mixing of the crystals within the composition. However, the distribution may also be homogeneous.

The luminescent crystals are up-converting particles that emit radiation at a wavelength in the visible or ultraviolet spectrum when irradiated with a radiation having a longer wavelength, and more particularly when irradiated with near-infrared radiation having a wavelength in the range of about 780 nm to about 1064 nm. The photoinitiator and the luminescent crystals are selected such that the emission wavelength of the luminescent crystals corresponds to the activation wavelength (i.e. at or near the peak absorption wavelength) of the photoinitiator.

Suitable luminescent crystals for use with exemplary embodiments of the present invention include those that employ lanthanide fluorides, fluoride salts, or oxide hosts, such as ytterbium fluoride salt (such as $Na(YbF_4)$) and/or lutetium oxide ($Lu_2O_3$), that are doped or co-doped with one or more lanthanide series ions, such as ytterbium ($Yb^{3+}$), lutetium ($Lu^{3+}$), thulium ($Tm^{3+}$), terbium ($Tb^{3+}$), erbium ($Er^{3+}$), and praseodymium ($Pr^{3+}$). Yttrium oxide and yttrium fluoride salt hosts are also contemplated, although lanthanide based hosts are preferred because of the lanthanide's contribution to the luminescent up-conversion. One preferred host is $Lu_2O_3$. Lutetium oxide has a lower phonon energy (300 $cm^-$) than yttrium fluoride but lutetium's ionic radii is nearly identical to that of the other lanthanide elements with which it is doped and all are in the plus three oxidation state. Closely matched ionic radii equates to more favorable dopant substitution within the host lattice. Further, $Lu_2O_3$ crystallizes in a cubic bixbyite structure which is more desirable that the sodium salt of yttrium tetrafluoride as a filler material for dental composites.

One particularly suitable luminescent crystal is lutetium oxide co-doped with ytterbium and thulium ($Lu_2O_3$:2%$Yb^{3+}$, 0.2% $Tm^{3+}$), described in Li, L. et. al., "Synthesis and up conversion luminescence of $Lu_2O_3$:$Yb^{3+}$,$Tm^{3+}$ crystals" Trans. Nonferrous Met. Soc. China 22(2012) 373-379, which is hereby incorporated by reference in its entirety. Other suitable luminescent crystals include $NaYbF_4$:$Tm^{3+}$, lutetium fluoride ($LuF_3$) co-doped with $Tm^{3+}$ and/or $Tb^{3+}$, as well as those described in Barrera, E. W., et al, "Emission properties of hydrothermal $Yb^{3+}$, $Er^{3+}$ and $Yb^{3+}$, $Tm^{3+}$-codoped Lu2O3 nanorods: upconversion, cathodoluminescence and assessment of waveguide behavior", Nanotechnology 22 (2011) and Li, C. et al., Shape controllable synthesis and upconversion properties of $NaYbF_4$/$NaYbF_4$:$Er^{3+}$ and $YbF_3$/$YbF_3$:$Er^{3+}$ microstructures", J. Mater. Chem., 18, 1353-1361 (2008), which are also incorporated herein by reference, all by way of example.

In co-doped Yb and Er, or Yb and Tm luminescent crystals such as $YbF_3$/$YbF_3$:$Er^{3+}$, the molar ratio could be from 1:1 to 1:10, respectively. The inverse ratios of 10:1 to 1:1, respectively, are also useful. The pH in which the crystal is formed can be used to change the shape. Having Yb as part of the matrix that will host either $Er^{3+}$ or $Tm^{3+}$ may have superior performance in other forms in which other rare earth metals are associated in the matrix, such as the co-doped salt $\beta$-$NaYF_4$:$Yb^{3+}$,$Tm^{3+}$ in which the percentages by weight are from 0.01 to 30% respectively and, again the inverse 30 to 0.01% respectively is also useful. In the oxide, co-doped crystals such as $LuO_3$: $Yb^{3+}$, $Tm^{3+}$ at the same weight percentages of the salt is useful.

The average particle size of the luminescent crystals is generally between 20 and 150 nm, typically between 30 and 80 nm, and may depend on what manufacturing process is used, although larger and smaller crystals are also contemplated. The crystal structure of the luminescent crystals may be spherical, rod-like, cylindrical, cubic, disk, hexagonal, or combinations thereof, as well as variety of other shapes.

Concentration of the absorption and emission centers, i.e., the dopants (for example $Yb^{3+}$ and $Tm^{3+}$ in the context of $Lu_2O_3$:2% $Yb^{3+}$, 0.2% $Tm^{3+}$), related to the efficiency of the up-conversion and thus the crystal's usefulness in dental composites. The efficiency and particle size may increase as a result of method of preparation and calcination of the crystals. With increasing calcination temperatures, up to 1100° C., the higher the temperature, the larger the particle and the more efficient the compound. Different methods and constituents, such as those described in the Li, C. and Barrera, E. W. articles already incorporated by reference, are exemplary of processes that can be used to produce different shapes and sizes of crystals.

Up-conversion is accomplished by way of a six step process, described (again in the context of $Lu_2O_3$:2% $Yb^{3+}$, 0.2% $Tm^{3+}$) with respect to FIG. 1. $Yb^{3+}$ ions are laser excited with 980 nm (102) emitting energy (105) that is absorbed by $Tm^{3+}$ at energy level $^3H_6$; the electron absorbs the energy and is excited to level $^3H_5$ (110). A non-emission decay then occurs and the electron drops from energy level $^3H_5$ to energy level $^3F_4$ (120). $Yb^{3+}$ is laser excited with 980 nm emitting energy that is absorbed by $Tm^{3+}$ at energy level $^3F_4$; the electron absorbs the energy and is excited to level $^3F_2$ (130). A non-emission decay then occurs and the electron drops from energy level $^3F_2$ to energy level $^3H_4$ (140). $Yb^{3+}$ is laser excited with 980 nm emitting energy that is absorbed by $Tm^{3+}$ at energy level $^3H_4$; the electron absorbs the energy and is excited to level $^1G_4$ (150). A minor portion of the electrons fall to the metastable energy level $^3F_4$ and emit photons at 653 nm while the majority of the electrons elevated to energy level $^1G_4$ fall to the ground energy level, $^3H_6$, emitting 490 nm photons in the process.

As shown with respect to Equations 1-3 below, when using $Lu_2O_3$ as the host matrix, examination of $Tm^{3+}$ demonstrates concentration quenching occurs above 0.2% dopant content. When $Tm^{3+}$ content is high, self-quenching or cross-relaxation mechanisms between $Tm^{3+}$ ions becomes active. The energy transfer processes can be described as depicted in the equations and such energy transfers can depopulate the $^1G_4$ levels but populate the $^3H_5$ levels shown in FIG. 1, leading to an increase in the extent of non-emission transitions. On the other hand, however, when $Yb^{3+}$ ions are heavily doped, many factors such as increased amount of impurities, concentration-quenching of $Yb^{3+}$, energy back transfer from $Tm^{3+}$ to $Yb^{3+}$ as depicted in Equation 4. Such back energy transfers effectively reduces up conversion emission intensity.

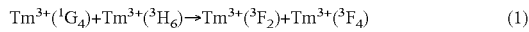

$$Tm^{3+}(^1G_4)+Tm^{3+}(^3H_6) \rightarrow Tm^{3+}(^3F_2)+Tm^{3+}(^3F_4) \qquad (1)$$

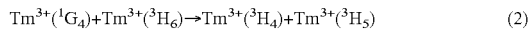

$$Tm^{3+}(^1G_4)+Tm^{3+}(^3H_6) \rightarrow Tm^{3+}(^3H_4)+Tm^{3+}(^3H_5) \qquad (2)$$

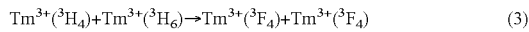

$$Tm^{3+}(^3H_4)+Tm^{3+}(^3H_6) \rightarrow Tm^{3+}(^3F_4)+Tm^{3+}(^3F_4) \qquad (3)$$

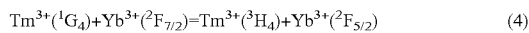

$$Tm^{3+}(^1G_4)+Yb^{3+}(^2F_{7/2})=Tm^{3+}(^3H_4)+Yb^{3+}(^2F_{5/2}) \qquad (4)$$

As for higher temperatures when calcinated in a $Lu_2O_3$: $Yb^{3+}$, $Tm^{3+}$ crystal, on FT-IR analysis the spectra shows the absorption bands of $OH^-$ become weaker with the increase of calcination temperature. $OH^-$ groups with high vibration frequency will increase the non-emission relaxation rate and hence decrease up conversion efficiency. This indicates that the enhanced up conversion intensity may come from the reducing of $OH^-$ groups, which are located on the surface of nanoparticles. By increasing the nanoparticles size using higher calcination temperatures the decrease of surface-to-volume ratio can reduce the $OH^-$ groups on the surface of nanoparticles.

Dental composites in accordance with exemplary embodiments may further include other additives in order to provide specifically desired features. Exemplary additives include ultra-violet stabilizers, fluorescent agents, opalescent agents, pigments, viscosity modifiers, fluoride-releasing agents, polymerization inhibitors, and the like. Typical polymerization inhibitors for a free radical system may include hydroquinine monomethyl ether (MEHQ), butylated hydroxytoluene (BHT), tertiary butyl hydro quinine (TBHQ), hydroquinone, phenol, and the like.

The amount of such additional additives is typically minor, such that the additives, together with the initiator and any accelerator, make up a total of not more than 1.5% by weight of the dental restorative composition.

The polymerization inhibitors may be present in amounts of from about 0.001 weight percent to about 1.5 weight percent of the dental restorative composition, such as from about 0.005 weight percent to about 1.1 weight percent or from about 0.01 weight percent to about 0.08 weight percent of the dental restorative composition.

Dental restorative compositions in accordance with exemplary embodiments can used to fill cavities of dental patients, resulting in a one-step placement and cure restorative composition not previously known in the art.

Figure 2:
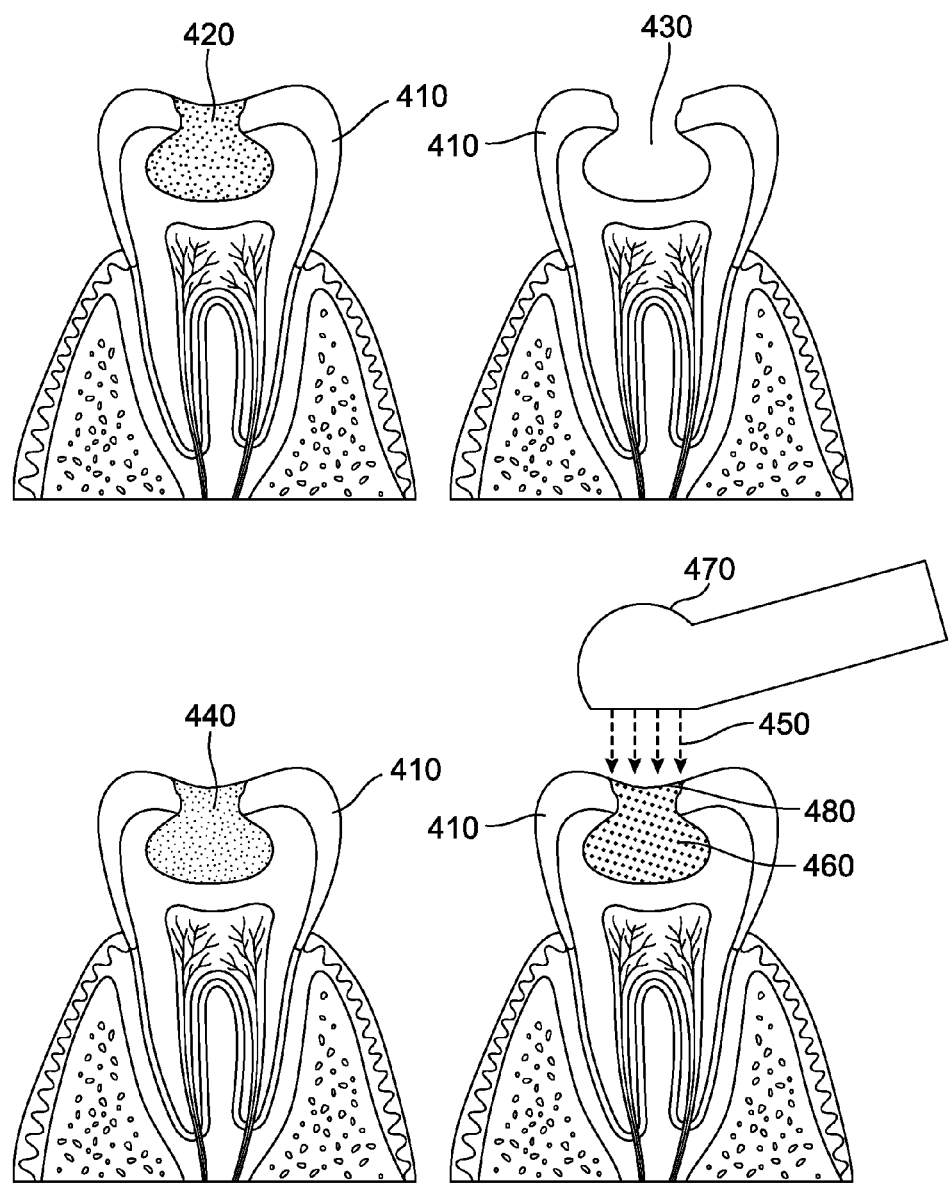
FIG. 2 schematically illustrates the curing process in accordance with exemplary embodiments.

Turning to FIG. 2, the curing process is schematically illustrated in the context of a dental application, in which a practitioner inspects the patient's tooth 410 and discovers tooth decay in the form of caries 420. The practitioner removes the caries 420 using standard practices and procedures, leaving behind a cavity 430 to be refilled. The practitioner applies and light cures dental adhesive, fills the cavity 430 with a dental restorative composition 440 in accordance with exemplary embodiments as described herein, for example one containing luminescent crystals of lutetium oxide co-doped with about 0.2% $Tm^{3+}$ and about 2% $Tb^{3+}$ and camphorquinone as the photoinitiator, along with the polymerizable resin and inert filler.

The luminescent crystals absorb near infrared radiation, including 980 nm in the case of lutetium oxide co-doped with 0.2% $Tm^{3+}$ and 2% $Tb^{3+}$ and, in response, also emit 490 nm visible blue radiation. The CQ is sensitive to the spectral emission wavelengths produced by the luminescent up conversion of the particles. Accordingly, when the practitioner applies 980 nm laser energy 450 using a curing light 470 having a laser diode that emits 980 nm 450, the luminescent crystals (shown as ref 460 for purposes of illustration) absorb the 980 nm laser radiation and emit a spectrum of light centered at 490 nm. This initiates the CQ and begins the polymerization process, causing the composite 440 to cure.

Any near-infrared radiation source may be employed in combination with appropriately matched NIR absorbing, up-converting luminescent crystals. However, those such as lutetium oxide co-doped with 0.2% $Tm^{3+}$ and 2% $Tb^{3+}$, that absorb a 980 nm wavelength radiation are presently preferred because that wavelength is currently readily available through relatively inexpensive diode lasers. It will be appreciated, however, that any laser source may be employed to generate the desired absorption wavelength of the luminescent crystals. For example, efficient fluorescent systems, pumped laser systems, and other pumped systems that generate longer wavelengths than the pump source may also be employed for use with matching luminescent crystal/photoinitiator pairs.

The depth of penetration of 980 nm radiation compared to that of 450 meter radiation (i.e. if the CQ in this example was initiated directly by the curing light) is up to 2.5 times greater or more through enamel and up to 5 times greater or more through dentin, resulting in the ability to cause initiation at locations deep within the composite after placement within a cavity and not heretofore possible. This provides a physical matrix very quickly, thereby locking in the size and shape of the composite providing less shrinkage by a factor of 10 and faster curing overall.

Although exemplary embodiments have been primarily described with a single wavelength as a "pump source" to cause emissions by the luminescent crystals, and which are applied in a constant manner, the disclosure is not so limited. The use of a visible radiation source in combination with near-infrared radiation is contemplated, but not preferred.

It will be appreciated that the source radiation may be modulated to achieve desired post cure physical properties for example, as described in U.S. Pat. No. 6,008,264 which is hereby incorporated by reference in its entirety and/or using multiple wavelengths simultaneously to achieve a desired therapeutic outcome and/or with multiple different photoinitiators.

For example, when the curing light or other radiation source is used to cure the dental restoration composite 440, the energy is delivered with two wavelengths applied simultaneously. This may be achieved, for example, using a curing light 470 that contains radiation sources of two separate wavelengths controlled by electronics capable of operating the radiation emitters independent of each other. In this case, the radiation sources are two laser diodes but one or both could be replaced with other radiation sources such as, but not limited to, Light Emitting Diodes.

Thus, two wavelengths such as 450 nm and 980 nm can both be employed. By way of further example, the 450 nm and 980 nm emitters are turned on at the same time at appropriate intensity, but with the 450 nm emitter pulsed in a triangular waveform for an "on" cycle period of 30 ms and an "off" cycle of 50 ms, while the 980 nm emitter is run continuously. The luminescent crystals absorb the 980 nm laser radiation and emit a spectrum of light centered at 490 nm deep within the composite as previously described, while the 450 nm pulsed radiation strikes and is absorbed by the surface 480 of the composite 440. The pulsing of the 450 nm on the surface of the composite can cause the surface to become harder and more wear resistant, while the deep absorption and emission by the luminescent crystals within the bulk of the composite result in a cured composite more flexible than the surface and that experiences less shrinkage.

According to another embodiment, the composite contains two photoinitiators, CQ as described in the other examples, as well as an acylphosphinate initiator that is sensitive at 405 nm wavelength. In this embodiment, the energy is delivered by three different wavelengths for which their respective sources are independently controllable by electronics cooperatively employed with or incorporated into the curing light 470. Here, the curing sequence is initiated when the 450 nm laser is pulsed in a square waveform for an "on" cycle period of 30 ms and an "off" cycle of 100 ms for a predetermined amount of time. The 980 and 405 nm radiation sources, in this case laser diodes, are run continuously to the completion of the prescribed curing time. The use of the additional initiator with the 405 nm activation wavelength can convert more monomers to polymers, thereby expanding the composite and/or reducing the shrinkage, and forming an overall stronger transverse tensile strength restoration.

It will be appreciated that these examples are not meant to be restrictive and there is a wide breadth of options available to mix initiators, luminescent crystals, down converting components such as fluorescing compounds, and down converting particles such as Er:YAG and Nd:YAG, along with mixed wavelength radiation all of which could be employed in combination with modulating source emission and wave forms.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material including dopants to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A dental restorative composite comprising:
   a polymerizable organic resin;
   a radiation activated initiator having an activation wavelength; an inert filler; and
   luminescent crystals, wherein the luminescent crystals emit radiation at a predetermined wavelength matching the initiator activation wavelength when the luminescent crystals are irradiated with radiation having a wavelength of at least 780 nm.

2. The dental restorative composite of claim 1, wherein the resin comprises a polymerizable (meth)acrylate.

3. The dental restorative composite of claim 2, wherein the resin comprises a compound selected from the group consisting of 2,2-bis[4-(2-hydroxy-3-methacryloyloxypropoxy)phenyl] propane, 1,6-bis(2-methacryloxyethoxycarbonylamino)-2,4,4-trimethylhexane, 2,2-bis[4-(methacryloyloxyethoxy)phenyl] propane (or ethoxylated bisphenol A-dimethacrylate), isopropyl methacrylate, triethyleneglycol dimethacrylate, diethyleneglycol dimethacrylate, tetraethyleneglycol dimethacrylate, 3-(acryloyloxy)-2-hydroxypropyl methacrylate, 1,3-propanediol dimethacrylate, 1,6-hexanediol di(meth)acrylate, pentaerythritol triacrylate, pentaerythritol tetraacrylate, pentaerythritol tetramethacrylate, and combinations thereof.

4. The dental restorative composite of claim 1, wherein the inert filler comprises strontium borosilicate, strontium fluoroalumino borosilicate glass, strontium alumino sodium fluoro phosphor-silicate glass, barium borosilicate, barium fluoroalumino borosilicate glass, barium aluminum-borosilicate glass, barium alumino borosilicate, calcium alumino sodium fluoro silicate, lanthanum silicate, lanthanum aluminosilicate, calcium alumino sodium fluoro phosphor silicate, silicon nitrides, titanium dioxide, fumed silica, colloidal silica, quartz, kaolin ceramics, calcium hydroxy apatite, zirconia, or mixtures thereof 5. The dental restorative composite of claim 1, wherein the radiation activated initiator has an activation wavelength in the range of about 360 nm to about 520 nm.

6. The dental restorative composite of claim 1, wherein the radiation activated initiator comprises camphorquinone, diketone initiators, derivatives of diketone initiators, acylphosphine oxide initiators, diphenyl (2, 4, 6-trimethylbenzoyl) phosphine oxide, 1-phenyl-1,2 propanedione, bis(2,4,6-trimethylbenzoyl)-phenylphospohine oxide, ethyl 2,4,6-trimethylbenzylphenyl phosphinate, or combinations thereof.

7. The dental restorative composite of claim 1, wherein the luminescent crystals comprise a crystalline host doped with a lanthanide series ion.

8. The dental restorative composite of claim 7, wherein the crystalline host is selected from the group consisting of lanthanide fluorides, lanthanide salts, lanthanide oxides, and combinations thereof.

9. The dental restorative composite of claim 8, wherein the crystalline host is co-doped with at least two different lanthanide series ions.

10. The dental restorative composite of claim 7, wherein the luminescent crystals comprise lutetium oxide co-doped with 2% ytterbium and 0.2% thulium having the formula $Lu_2O_3:2\%Yb^{3+}, 0.2\%Tm^{3+}$.

11. The dental restorative composite of claim 7, wherein the crystalline host is doped with not more than 5% lanthanide series ion.

12. The dental restorative of claim 7, wherein the luminescent crystals have a geometry selected from the group consisting of spheres, cubes, rods, cylinders, and combinations thereof.

13. The dental restorative of claim 7, wherein the luminescent crystals have a particle size in the range of 20 nm to 150 nm.

14. The dental restorative of claim 7, wherein the crystalline host is a lanthanide fluoride, lanthanide salt, or lanthanide oxides doped with a lanthanide series ion encased within the host.

15. A method of curing a dental restorative composite comprising:
  providing a dental restorative composite of claim 1;
  filling a cavity formed in a tooth with the provided dental restorative composite; and
  irradiating the dental restorative composite with radiation from a laser source that emits radiation at a pre-determined fixed wavelength in the near-infrared range of the spectrum to initiate curing of the dental restorative compound, wherein the emitted radiation at the pre-determined fixed wavelength causes the luminescent crystals to emit radiation at the activation wavelength of the initiator.

16. The method of claim 15, wherein the laser source emits radiation at a wavelength of 980 nm.

17. The method of claim 16, wherein the laser source is a laser diode.

18. The method of claim 15, further comprising irradiating the dental restorative composite with radiation from a second radiation source that emits radiation at a second pre-determined fixed wavelength different from the pre-determined fixed wavelength in the near-infrared range of the spectrum.

19. The method of claim 18, wherein the dental restorative composite is provided having a second radiation activated initiator with a second activation wavelength.

20. The method of claim 15, wherein the step of irradiating comprises irradiating with at least two different waveforms.

21. The method of claim 20, wherein the first waveform is a single pulse of a first power and the second waveform is a square wave at a second power less than the first power applied for a longer duration than the first waveform, wherein the first and second waveforms are separated by a period of time in which no radiation is emitted from the laser source toward the composite.

22. A dental restorative composite comprising:
  about 15 to about 25 percent by weight of a polymerizable organic (meth)acrylate resin;
  about 0.05 to about 1.0 percent by weight of a radiation activated initiator selected from the group consisting of camphorquinone, diketone initiators, derivatives of diketone initiators, acylphosphine oxide initiators, diphenyl (2, 4, 6-trimethylbenzoyl) phosphine oxide, 1-phenyl-1,2 propanedione, bis(2,4,6-trimethylbenzoyl)-phenylphospohine oxide, ethyl 2,4,6-trimethylbenzylphenyl phosphinate, and combinations thereof;
  about 56% to about 85% by weight of an inert filler; and
  about 1% to about 20% by weight luminescent crystals comprising a crystalline host selected from the group consisting of lanthanide fluorides, lanthanide salts, lanthanide oxides, and combinations thereof doped with a lanthanide series ion, wherein the luminescent crystals emit radiation at a predetermined wavelength matching the initiator activation wavelength when the luminescent crystals are irradiated with near-infrared radiation having a wavelength in the range of about 780nm to about 1064 nm.

* * * * *